(12) United States Patent
Kawamura (10) Patent No.: US 9,642,772 B2
(45) Date of Patent: May 9, 2017

(54) MEDICAL CONTAINER

(71) Applicant: DAIKYO SEIKO, LTD., Tokyo (JP)

(72) Inventor: Hideaki Kawamura, Tokyo (JP)

(73) Assignee: DAIKYO SEIKO, LTD., Tokyo (JP)

( * ) Notice: Subject to any disclaimer, the term of this patent is extended or adjusted under 35 U.S.C. 154(b) by 0 days.

(21) Appl. No.: 14/734,523

(22) Filed: Jun. 9, 2015

(65) Prior Publication Data

US 2015/0366754 A1 Dec. 24, 2015

(30) Foreign Application Priority Data

Jun. 23, 2014 (JP) ................................. 2014-127984

(51) Int. Cl.
*A61J 1/03* (2006.01)
*B29C 45/14* (2006.01)
(Continued)

(52) U.S. Cl.
CPC ............. *A61J 1/03* (2013.01); *A61B 10/0096* (2013.01); *A61J 1/065* (2013.01);
(Continued)

(58) Field of Classification Search
CPC ......... A61J 1/03; A61J 1/065; B29C 66/1224; B29C 66/73921; B29C 65/72;
(Continued)

(56) References Cited

U.S. PATENT DOCUMENTS 739,616 A 9/1903 Oxley
4,227,615 A * 10/1980 Flick ...................... B65D 25/54
200/82 R
(Continued)

FOREIGN PATENT DOCUMENTS

DE 871963 4/1953
EP 1433584 6/2004
(Continued)

*Primary Examiner* — Anthony Stashick
*Assistant Examiner* — Ernesto Grano
(74) *Attorney, Agent, or Firm* — Hamre, Schumann, Mueller & Larson, P.C.

(57) ABSTRACT

The present invention provides a medical container: that is configured of an upper member and a lower member; that can be molded by injection molding; that has an excellent dimensional accuracy; and in addition to these, that is capable of effectively preventing the trouble that a molten resin for joining the upper member and the lower member enters the container. The present invention is a bottomed tubular medical container 1 made of a resin and continuously configured of a neck 12, a shoulder 14, and a body 16. The medical container 1 includes an upper member 2 and a lower member 4 each having a structure obtained by vertically dividing the medical container 1, a circular recess is formed at a circular lower end face of the upper member 2 along a shape of the lower end face, and in the lower member 4, a circular projection is formed at a circular upper end face of the lower member 4 along a shape of the upper end face, the circular projection of the lower member 4 is interference-fitted to the circular recess of the upper member 2, further, a fitting portion between the circular projection and the circular recess is sealed with a molten resin 6 from an outer circumferential side of the medical container 1, and the upper member 2 and the lower member 4 are fixed with the molten resin 6.

5 Claims, 5 Drawing Sheets

(51) Int. Cl.

| | | |
|---|---|---|
| *A61J 1/06* | (2006.01) | |
| *B65D 8/00* | (2006.01) | |
| *A61B 10/00* | (2006.01) | |
| *B29C 65/42* | (2006.01) | |
| *B29C 65/48* | (2006.01) | |
| *B29C 65/56* | (2006.01) | |
| *B29C 65/72* | (2006.01) | |
| *B29C 65/00* | (2006.01) | |
| *B29K 101/12* | (2006.01) | |
| *B29C 45/16* | (2006.01) | |
| *B29K 23/00* | (2006.01) | |
| *B29L 31/00* | (2006.01) | |
| *A61J 1/05* | (2006.01) | |

(52) U.S. Cl.
  CPC ........ B29C 45/14467 (2013.01); B29C 65/42 (2013.01); B29C 65/4815 (2013.01); B29C 65/565 (2013.01); B29C 65/72 (2013.01); B29C 66/0382 (2013.01); B29C 66/1224 (2013.01); B29C 66/1226 (2013.01); B29C 66/542 (2013.01); B29C 66/73921 (2013.01); B65D 11/04 (2013.01); *A61J 1/05* (2013.01); *B29C 45/16* (2013.01); *B29C 66/71* (2013.01); *B29K 2023/38* (2013.01); *B29K 2101/12* (2013.01); *B29L 2031/716* (2013.01)

(58) Field of Classification Search
  CPC .............. B29C 66/1226; B29C 66/542; B29C 66/0382; B29C 65/4815; B29C 45/14467; B29C 45/16; B29C 45/00; B29C 45/0062; B29L 2031/716; B65D 11/04; B29K 2023/38; B29K 2101/12

USPC .......................................................... 215/252
  See application file for complete search history.

(56) References Cited

U.S. PATENT DOCUMENTS

| | | | | |
|---|---|---|---|---|
| 7,434,702 | B2* | 10/2008 | Yaita | ................... B29C 45/0062 215/274 |
| 9,061,801 | B2* | 6/2015 | Ropele | ............... B29C 45/1635 |
| 2004/0134871 | A1* | 7/2004 | Yaita | ................... B29C 45/0062 215/43 |
| 2005/0061706 | A1* | 3/2005 | Reynolds | ............... B65D 11/04 206/540 |
| 2007/0071924 | A1* | 3/2007 | Archeny | ............. B29C 49/4278 428/35.7 |
| 2010/0116770 | A1* | 5/2010 | Thomasset | ................ B32B 1/02 215/12.2 |
| 2010/0230405 | A1* | 9/2010 | Strait, III | ................ B29C 65/08 220/4.01 |
| 2011/0253713 | A1* | 10/2011 | Ichikawa | ................ B29C 45/14 220/62.11 |
| 2011/0309083 | A1* | 12/2011 | Hsiu-Tzu Charlene | ................... A45D 34/00 220/505 |
| 2013/0026164 | A1* | 1/2013 | Lingel | ................ B29C 66/112 220/4.01 |

FOREIGN PATENT DOCUMENTS

| | | |
|---|---|---|
| GB | 640516 | 7/1950 |
| JP | 52-101180 | 8/1977 |
| JP | 2002-029538 | 1/2002 |
| JP | 2004-217311 | 8/2004 |
| JP | 2010-280089 | 12/2010 |

* cited by examiner

MEDICAL CONTAINER

TECHNICAL FIELD

The present invention relates to a bottomed tubular medical container made of a resin and continuously configured of a neck, a shoulder, and a body. More specifically, the present invention relates to a medical container comprising an upper member and a lower member each having a structure obtained by vertically dividing the medical container.

BACKGROUND ART

Conventionally, a resin-made medical container such as a vial has generally been molded by blow molding. However, since the blow molding is a molding method that does not use an inner mold, there has been a problem that the wall thickness of the container is liable to be uneven and the dimensional reproducibility is low.

A method of molding the medical container by injection molding has been known as a measure for solving the problem. Since the injection molding is a molding method that uses an inner mold and an outer mold, there is an advantageous point that it is easy to make the wall thickness of the container even and thus the dimensional reproducibility is high. However, die cutting of the inner mold cannot be conducted in the case of a container such as a vial in which the diameter on the opening side is smaller than the diameter on the body side, and molding the medical container cannot be conducted by the injection molding without some improvement. Thus, a method in which an upper member and a lower member each having a structure obtained by vertically dividing a container are separately injection-molded and thereafter the upper member and the lower member are integrally bound has been proposed.

For example, a method for producing a plastic bottle in which a bottomed tubular main body and a tubular head having a shoulder and a neck are separately molded with a metal mold, and the resultant main body-molded article and a head-molded article are joined with an organic solvent or by ultrasonic has been proposed in Japanese Patent Laid-Open No. 2002-029538.

Moreover, a method for molding a synthetic resin container, in which, when molding a container having different diameters at a body and a mouth, a bottomed tubular body member and a mouth member having a shoulder are separately injection-molded, the lower end of the mouth member is joined to the upper end of the body opening in such a manner that both ends are fitted, and a molten resin is injected in a ring shape along the fitted shoulder to conduct seal molding has been proposed in Japanese Patent Laid-Open No. 52-101180.

Further, as a method for producing a resin-made bottle container in which a tubular neck having a diameter smaller than a diameter of a bottomed tubular body is provided at an upper end of the body, a method for producing a resin-made bottle container, in which an upper side portion and a lower side portion having a shape obtained by vertically dividing the bottle container into two portions at the upper end or the lower end of the body are separately molded with a resin by injection molding, thereafter, in a state where respective divided ends of the upper side portion and the lower side portion are joined, the joined face of the respective parts is shielded from outside, a molten resin is injected by insert molding in a fluid-tight manner, the molten resin is cooled and solidified to make a cover member, and the upper part and the lower part are integrated with the cover member has been proposed in Japanese Patent Laid-Open No. 2004-217311.

Furthermore, as a cosmetic container having a container main body and a lid, a cosmetic container in which the container main body consists of a neck member, a body member, and a connecting member for connecting the two members, a fitting groove for fitting the neck and a body projection protruding from the circumference of the fitting groove are formed at the upper end of the body member, a neck projection is formed in the neck member so as to be adjacent to the body projection when the neck member is fitted to the body member, and the body member and the neck member are welded and fixed with the connecting member formed by a molten resin injected to the upper end of the body member passing through the body projection and the neck projection has been proposed in Japanese Patent Laid-Open No. 2010-280089.

SUMMARY OF INVENTION

Technical Problem

However, since the production method described in Japanese Patent Laid-Open No. 2002-029538 is a method in which the main body-molded article and the head-molded article are joined with an organic solvent or by ultrasonic, there has been a problem that the production efficiency is low because facilities such as an ultrasonic generation apparatus become separately needed, which makes the production process complicated.

In the technologies described in Japanese Patent Laid-Open No. 52-101180, Japanese Patent Laid-Open No. 2004-217311, and Japanese Patent Laid-Open No. 2010-280089, since the body member or the like and the mouth member or the like are joined with the molten resin, there has been a problem that the molten resin may enter the container although the joining strength between the body member or the like and the mouth member or the like is relatively high. In the case where the molten resin enters the container (hereinafter, such trouble is sometimes written as "resin leak"), it is not preferable in that the appearance becomes poor and there is a risk that an impression as if a problem in product quality exists is given even though there is actually no problem in product quality of the container or the contents thereof. Moreover, the medical containers among resin-made containers have a characteristic that they are often configured of cyclic olefin based polymers having excellent chemical resistance and non-adsorptive property, such as cycloolefin polymers (COP) and cycloolefin copolymers (COC). In the container configured of the COP or COC, it is not desirable from the standpoint of maintaining product quality of medical containers that a resin other than the COP or COC is used as the molten resin because there is a risk that the product quality of the medical container is degraded when the molten resin enters the container.

The present invention has been made in order to solve the problems of the conventional technologies. That is to say, the present invention provides a medical container: that is configured of an upper member and a lower member; that can be molded by injection molding; that has an excellent dimensional accuracy; and in addition to these, that is capable of effectively preventing the trouble that a molten resin for joining the upper member and the lower member enters the container.

Solution to Problem

The present inventors have conducted diligent studies in order to solve the problems to find out that the problems can be solved by forming a circular recess at a lower end face of the upper member, forming a circular projection at an upper end face of the lower member, and interference-fitting (also referred to as "positive fitting") the circular projection to the circular recess, and have completed the present invention.

That is to say, according to the present invention, a bottomed tubular medical container made of a resin and continuously configured of: a tubular neck comprising an opening formed on an upper end thereof; a trumpet-shaped shoulder whose diameter expands as the diameter goes toward a lower end of the shoulder; and a bottomed tubular body having a diameter larger than a diameter of the neck and comprising a bottom at a lower end thereof, the medical container comprising: an upper member; and a lower member, each having a structure obtained by vertically dividing the medical container along a direction perpendicular to a central axis of the medical container, wherein the upper member is configured so as to comprise at least the neck and the shoulder, and a circular recess is formed at a circular lower end face of the upper member along a shape of the lower end face, the lower member is configured by a portion or the whole of the body, and a circular projection is formed at a circular upper end face of the lower member along a shape of the upper end face, the circular projection of the lower member is interference-fitted to the circular recess of the upper member, further, a fitting portion between the circular projection and the circular recess is sealed with a molten resin from an outer circumferential side of the medical container, and the upper member and the lower member are fixed with the molten resin is provided.

It is preferable that the medical container of the present invention is a medical container in which both the circular recess of the upper member and the circular projection of the lower member are formed in a tapered shape toward the upper end side, and the circular projection is fitted to the circular recess so as to bring the tapered face of the circular recess and the tapered face of the circular projection into contact.

Moreover, it is preferable that the medical container of the present invention is a medical container in which the circular recess of the upper member is a cutout recess having a structure formed by cutting out an inner circumferential side of the upper member, the circular projection of the lower member is a cutout projection formed by a residual portion left after cutting out an outer circumferential side of the lower member, a circular groove is formed on an outer circumferential side of the medical container along a circumferential direction of the medical container by making a height of the cutout projection larger than a depth of the cutout recess, a fitting portion between the cutout projection and the cutout recess is sealed with the molten resin from the outer circumferential side of the medical container by filling the molten resin in the circular groove, and the upper member and the lower member are fixed with the molten resin.

Advantageous Effects of Invention

The medical container of the present invention is configured of an upper member and a lower member, can be molded by injection molding, has an excellent dimensional accuracy, and in addition to these, the medical container of the present invention is capable of effectively preventing the trouble that a molten resin for joining the upper member and the lower member enters the container.

BRIEF DESCRIPTION OF DRAWINGS

The preferred embodiments according to the invention will be described below with reference to the appended drawings, wherein.

DESCRIPTION OF EMBODIMENTS

Hereinafter, the present invention will be described with reference to appended drawings. However, the present invention is not limited to the following embodiments, and includes all objects having matters used to specify the invention. In addition, there sometimes occurs the case where the same reference signs are given to the members having the same structure in the drawings and the explanation is omitted.

Figure 1:
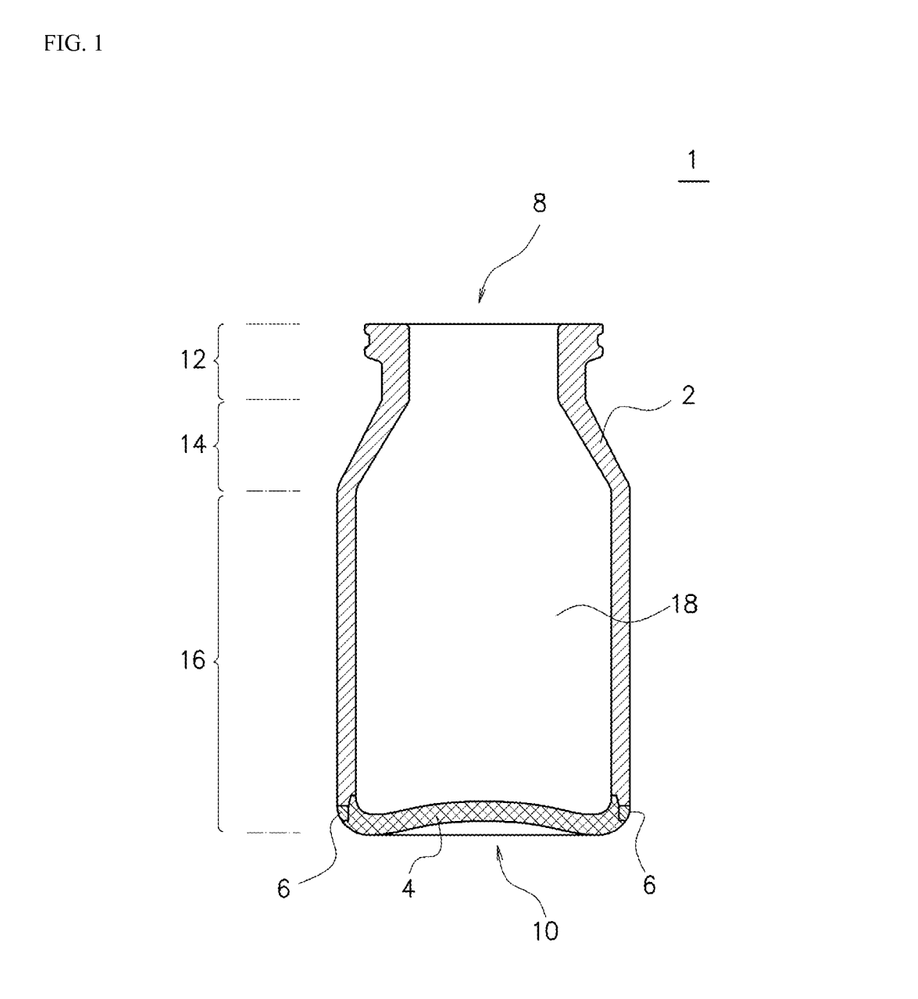
FIG. 1 is a sectional view schematically illustrating a section obtained by cutting the medical container of the present invention so as to pass through a central axis thereof.

[1] Medical Container:

FIG. 1 is a sectional view schematically illustrating a section obtained by cutting the medical container of the present invention so as to pass through the central axis thereof. The medical container 1 illustrated in FIG. 1 is a medical vial (bottle). However, the "medical container" of the present invention is not limited to vials. That is to say, a medical container to be used in medical use is sufficient as the "medical container" of the present invention, and the "medical container" here means articles in general to be vessels in which a liquid medicine or specimen is stored, transported, or mixed regardless of their names.

[2] Entire Shape:

The medical container 1 illustrated in FIG. 1 is a bottomed tubular medical container continuously configured of a neck 12, a shoulder 14, and a body 16.

[2-1] Bottomed Tubular Shape:

The medical container 1 illustrated in FIG. 1 is configured in a bottomed-and-cylindrical shape in such a manner that an opening 8 is formed at an upper end thereof and a bottom 10 is provided at a lower end thereof. Moreover, the medical container 1 is formed in a differential-diameter cylindrical shape in which the diameter of the neck 12 and the diameter of the body 16 are different. Further, the medical container 1 is a medical container in which a cavity 18 is partitioned on an inner circumferential side of an outer wall thereof.

However, a shape: in which a cavity is partitioned on an inner circumferential side of an outer wall; and which has a bottom that blocks one end is sufficient for "bottomed and cylindrical shape", and the shape is not limited to the shape illustrated in FIG. 1. The shape may be square cylindrical that is different from cylindrical shape, and may also be a shape in which the outer diameter, the inner diameter, the wall thickness of the outer wall, or the like is changed toward upward and downward directions.

[2-2] Neck:

The neck 12 of the medical container 1 illustrated in FIG. 1 is configured in a tubular shape in which the opening 8 is formed at an upper end thereof. In the neck 12, a cylindrical portion (lip portion) having a thick thickness is formed at the circumference of the opening 8, and a cylindrical portion having a thin thickness and the lower end of the lip portion are continuously formed. Moreover, the lower end of the cylindrical portion having a thin thickness and the upper end of the shoulder 14 are continuously formed.

However, the shape of the neck is not limited to the shape illustrated in FIG. 1. For example, the shape of the neck may be a shape in which the lip portion is formed so as to directly connected to the shoulder and the lip portion does not have the cylindrical portion having a thin thickness (namely, the neck is configured of only the lip portion).

[2-3] Shoulder:

The shoulder 14 of the medical container 1 illustrated in FIG. 1 is configured in a trumpet shape so that the diameter expands as the diameter goes toward a lower end of the shoulder. The shoulder 14 is a portion through which the neck 12 having a smaller diameter and the body 16 having a larger diameter are connected. That is to say, the upper end of the shoulder 14 and the lower end of the neck 12 (namely, the lower end of the cylindrical portion having a thin thickness) are continuously configured, and the lower end of the shoulder 14 and the upper end of the body 16 are continuously configured. In the medical container 1 illustrated in FIG. 1, since the body 16 is formed so that the thickness thereof is further thinner than the thickness of the thin cylindrical portion constituting the lower end side of the neck 12, the shoulder 14 is configured so that the thickness on the side of the neck 12 is thicker and the thickness gradually becomes thinner as the thickness goes toward the lower end side. Moreover, the shoulder 14 is formed in a hollow truncated cone shape.

However, the shape of the shoulder is not limited to the shape illustrated in FIG. 1. For example, the thickness may be the same from the upper end to the lower end, or the shape of the shoulder is not the hollow truncated cone shape, but may be configured in a bowl shape in which the outer wall is curved so as to be upwardly projected, or may be configured in a bell shape in which the outer wall is curved so as to be downwardly recessed.

[2-4] Body:

The body 16 of the medical container 1 illustrated in FIG. 1 is configured so as to have a larger diameter than the body 12 in a bottomed tubular shape including a bottom 10 at a lower end thereof. The upper end of the body 16 and the lower end of the neck 12 are continuously configured. The expression "having a larger diameter than the neck" means that the inner diameter of the body is larger than the inner diameter of the neck. The bottom 10 is formed in an arch shape so as to be upwardly projected.

However, the shape of the body is not limited to the shape illustrated in FIG. 1. For example, the shape of the bottom is not the arch shape, but the bottom may be formed in a flat plate shape.

[2-5] Size:

The medical container 1 illustrated in FIG. 1 is a vial having a volume of 20 mL. The medical container 1 is configured so as to have a height of 60.52 mm, an inner diameter of the neck 12 of 12.50 mmϕ, an outer diameter of the body 16 of 30.0 mmϕ, and a thickness of the body 16 of 1.8 mm.

However, the size of the medical container 1 is not limited to the same size as the size of the medical container 1 in FIG. 1. For example, the constitution of the present invention is applicable to medical containers having a volume of 2 mL to 10,000 mL.

[3] Constituent Material

The medical container 1 illustrated in FIG. 1 is made of a cycloolefin polymer (COP). However, the constituent material for the medical container may be a resin, and is not limited to the COP. Specific materials are not particularly limited, however the constituent material is preferably a thermoplastic hard resin that has an excellent mechanical strength and makes it possible to mass-produce a molded article at low cost. Examples of the constituent material include cyclic olefin based resins, polyethylene (PE) based resins, polypropylene (PP) based resins, polycarbonate (PC) based resins, polyvinyl chloride (PVC) based resins, and so on. Among these resins, the cyclic olefin based resins having a low elution property and excellent transparency and gas barrier property are preferable, and the COP is particularly preferable. In addition, the term "(poly) X based resin" in the present specification includes not only a single polymer of X but also copolymers of X. That is to say, the cycloolefin copolymers (COC) in addition to the COPs are included in the cyclic olefin based resins.

[4] Constituent Members:

The constituent members consists of the upper member 2 and the lower member 4, each having a structure obtained by vertically dividing the medical container 1 along a direction perpendicular to a central axis of the medical container.

Figure 2:
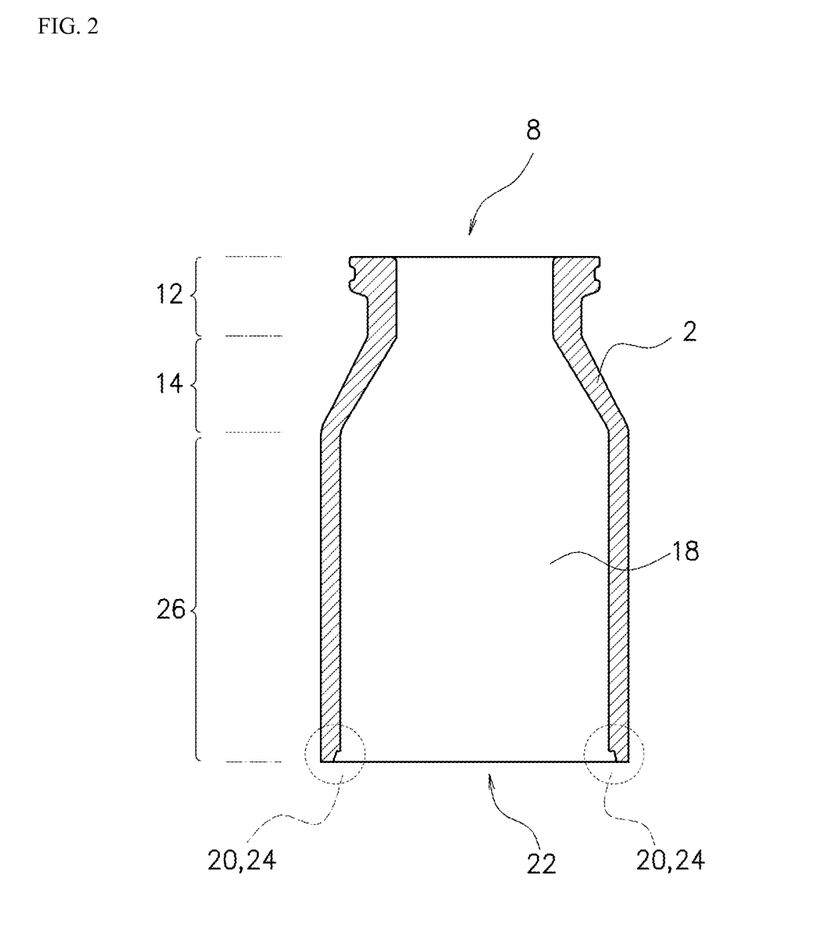
FIG. 2 is a sectional view schematically illustrating a section obtained by cutting an upper member illustrated in FIG. 1 so as to pass through a central axis thereof.

[4-1] Upper Member:

FIG. 2 is a sectional view schematically illustrating a section obtained by cutting the upper member so as to pass through the central axis thereof. The upper member 2 illustrated in FIG. 2 constitutes the neck 12, the shoulder 14, and a portion of the body 16 (a portion excluding the bottom 10, tubular body 26). And a lower opening 22 is formed on the lower end side of the upper member 2.

However, the upper member may be configured so as to include at least the neck and the shoulder. Taking the medical container 1 illustrated in FIG. 1 as an example, a parting line between the upper member 2 and the lower member 4 may exist anywhere from the boundary line between the shoulder 14 and the body 16 to the lower end of the medical container 1. That is to say, the medical container 1 may be vertically divided anywhere in the body 16. By taking such a structure, it is made possible to conduct die-cutting of the inner mold.

In the upper member 2 illustrated in FIG. 2, the circular recess 20 is formed at the circular lower end face along the shape of the lower end face. The term "circular" here denotes a shape of the section obtained by cutting the medical container at the parting line in the direction perpendicular to the central axis. The circular projection of the lower member is fitted to the circular recess 20.

Examples of the structure of the circular recess of the upper member include a cutout recess or the like having a structure obtained by cutting out the outer circumferential side of the upper member. However, in the present invention, it is preferable that the circular recess 20 of the upper member 2 is a cutout recess 24 having a structure obtained by cutting out the inner circumferential side of the upper member 2 as illustrated in FIG. 2. Such a structure, when compared with the cutout recess having a structure obtained by cutting out the outer circumferential side of the upper member 2, is preferable in that when secondary molding (secondary injection) that will be mentioned later is conducted, the upper member 2 is hard to deform by the pressure of the secondary molding.

Figure 3:
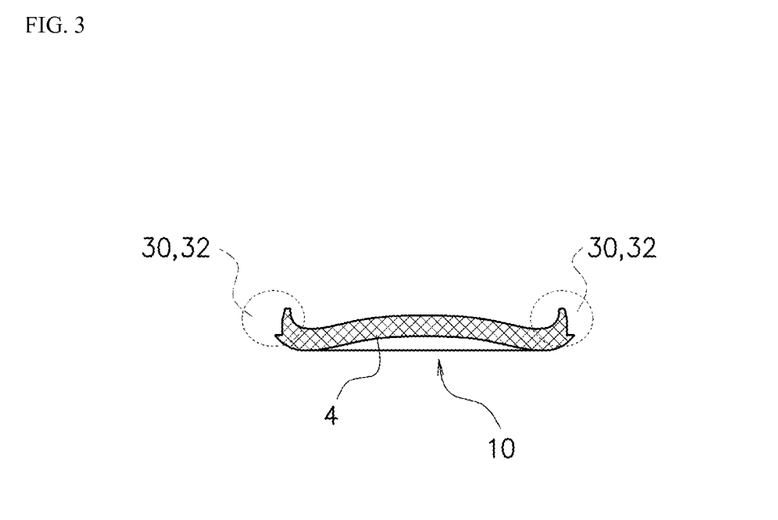
FIG. 3 is a sectional view schematically illustrating a section obtained by cutting a lower member illustrated in FIG. 1 so as to pass through a central axis thereof.

[4-2] Lower Member:

FIG. 3 is a sectional view schematically illustrating a section obtained by cutting the lower member so as to pass through the central axis thereof. The lower member 4 illustrated in FIG. 3 constitutes a portion of the body 16 (bottom 10). However, the lower member may constitute the whole body. That is to say, the parting line between the upper member 2 and the lower member 4 may exist on the boundary line between the shoulder 14 and the body 16 as in the medical container 1 illustrated in FIG. 1. Die-cutting of the inner mold is possible even for such a structure.

In the lower member 4 illustrated in FIG. 3, the circular projection 30 is formed at the circular upper end face along the shape of the upper end face. The definition of the term "circular" is the same as in the case of the upper member. The circular projection 30 is fitted to the circular recess 20 of the upper member 2.

Examples of the circular projection of the lower member include a cutout projection or the like formed by a residual portion left after cutting out an inner circumferential side of the lower member. However, in the present invention, it is preferable that the circular projection 30 of the lower member 4 is a cutout projection 32 formed by a residual portion left after cutting out the outer circumferential side of the lower member 4 as illustrated in FIG. 3. Such a structure, when compared with the cutout projection having a structure formed by a residual portion left after cutting out the inner circumferential side of the lower member 4, is preferable in that when the secondary molding (secondary injection) that will be mentioned later is conducted, the upper member 2 is hard to deform by the pressure of the secondary molding.

Figure 4A:
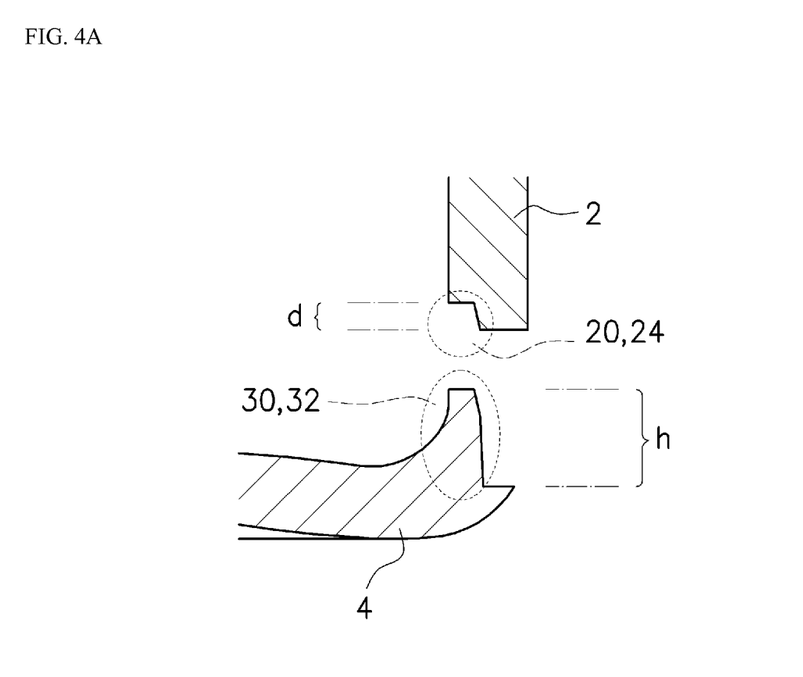
FIG. 4A is a process drawing schematically illustrating a state before fitting the lower member to the upper member in a production process of the medical container illustrated in FIG. 1.
Figure 4B:
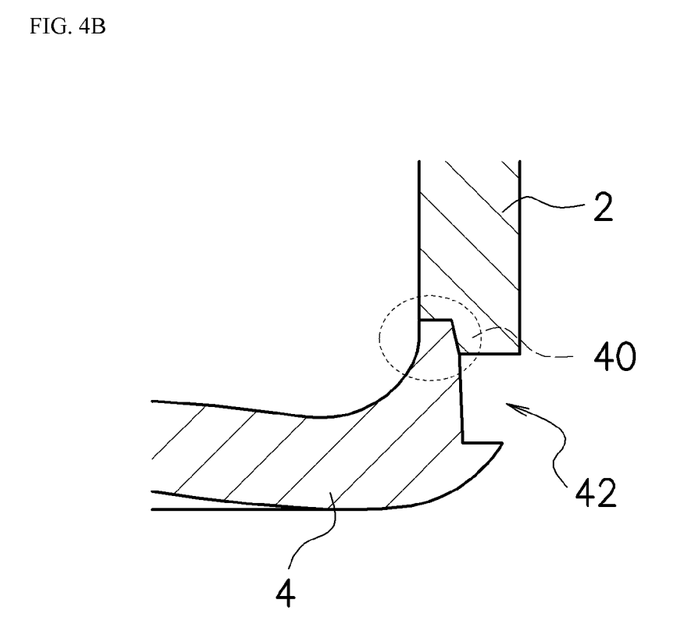
FIG. 4B is a process drawing schematically illustrating a state at the time when the lower member is fitted to the upper member in the production process of the medical container illustrated in FIG. 1.
Figure 4C:
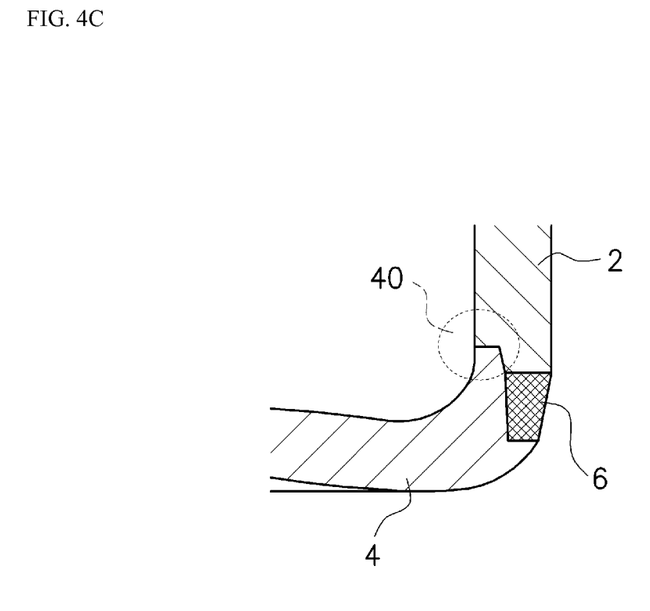
FIG. 4C is a process drawing schematically illustrating a state after fitting the lower member to the upper member and sealing the fitting portion with a molten resin in the production process of the medical container illustrated in FIG. 1.

[5] Bonding Structure:

Any of FIG. 4A to FIG. 4C is a diagram showing the production processes of the medical container of the present invention, and the vicinity of the fitting portion between the upper member and the lower member is enlarged and shown. FIG. 4A is a process drawing schematically illustrating a state before fitting the lower member to the upper member, FIG. 4B is a process drawing schematically illustrating a state at the time when the lower member is fitted to the upper member, and FIG. 4C is a process drawing schematically illustrating a state after fitting the lower member to the upper member and sealing the fitting portion with a molten resin. Hereinafter, the bonding structure between the upper member and the lower member of the medical container of the present invention will be described with reference to these drawings.

[5-1] Structure of Fitting Portion Between Upper Member and Lower Member:

It is preferable that both the circular recess 20 (cutout recess 24) of the upper member 2 and the circular projection 30 (cutout projection 32) of the lower member 4 are formed in a tapered shape toward the upper end side as illustrated in FIG. 4A. By taking such a structure, it becomes easy to fit the circular projection 30 to the circular recess 20 and it becomes possible to easily conduct interference-fitting that will be mentioned later.

The taper of the circular recess 20 and the circular projection 30 illustrated in FIG. 4A is a taper having an angle of 10°. However, the angle of the taper is not particularly limited, and can appropriately be selected within a range from an angle of 1° to 45°. It is preferable that the angle of the taper is set in a range from 3° to 25° from the standpoint of making it easy to fit the circular projection 30 to the circular recess 20, strengthening the state of fitting between the circular recess 20 and the circular projection 30, and preventing the trouble that the molten resin enters the container.

Moreover, it is preferable that the cutout recess 24 of the upper member 2 and the cutout projection 32 of the lower member 4 are configured so that the height h of the cutout projection 32 is larger than the depth d of the cutout recess 24 as illustrated in FIG. 4A. By taking such a structure, the circular grove 42 can be formed on the outer circumferential side of the medical container 1 along the circumferential direction when the cutout projection 32 of the lower member 4 is fitted to the cutout recess 24 of the upper member 2 as illustrated in FIG. 4B. The circular groove 42 functions as a gate when the molten resin is filled, and the upper member 2 and the lower member 4 can be bound by sealing the fitting portion 40 between the circular projection (cutout projection) and the circular recess (cutout recess) from the outer circumferential side of the medical container with the molten resin 6 as illustrated in FIG. 4C.

[5-2] Interference-Fitting:

In the medical container 1 illustrated in FIG. 1, the circular projection 30 of the lower member 4 is interference-fitted to the circular recess 20 of the upper member 2 as illustrated in FIG. 4B. The "Interference-fitting" means that the circular projection 30 having an outer diameter larger than the inner diameter of the circular recess 20 is fitted. By the interference-fitting, the contact faces (fitting faces) of the circular projection and the circular recess can be adhered extremely firmly due to the flexibility of the circular projection and the circular recess, and the resin leak of the molten resin can effectively be prevented.

The medical container 1 illustrated in FIG. 1 is formed so as to have an inner diameter of the circular recess 20 of 27.46 mmϕ, an outer diameter of the circular projection 30 of 27.51 mmϕ, and an interference of 0.05 mm. However, the structure for interference-fitting is not limited to such a structure. The interference may appropriately be selected within a range from 0.02 mm to 0.30 mm.

It is preferable in the medical container 1 illustrated in FIG. 1 that the circular projection 30 is fitted to the circular recess 20 so as to bring the taper face of the circular projection 30 and the taper face of the circular recess 20 into contact as illustrated in FIG. 4B. Such a structure is preferable in that it becomes easy to fit the circular projection 30 to the circular recess 20 and interference-fitting can easily be conducted.

[5-3] Sealing with Molten Resin

In the medical container 1 illustrated in FIG. 1, the fitting portion 40 between the circular projection and the circular recess is sealed with the molten resin 6 from the outer circumferential side of the medical container, and the upper member 2 and the lower member 4 are fixed with the molten resin 6 as illustrated in FIG. 4C. That is to say, when the molten resin obtained by heat-melting is filled in the circular groove 42 illustrated in FIG. 4B, the molten resin 6 makes contact with both the upper member 2 and the lower member 4 to exhibit adhesion to the upper member 2 and lower member 4 as illustrated in FIG. 4C. By cooling and solidifying the molten resin 6, the fitting portion 40 between the circular projection and the circular recess can be sealed with the molten resin 6 from the outer circumferential side of the medical container. Such a structure is preferable because the upper member 2 and the lower member 4 are firmly fixed with the molten resin 6 in addition to the fact that the circular projection 30 of the lower member 4 is interference-fitted to the circumferential recess 20 of the upper member 2. Moreover, since the circular projection 30 of the lower member 4 is interference-fitted to the circular recess 20 of the upper member 2, the molten resin 6 never enters the fitting portion 40 and resin leak can effectively be prevented. In addition, the "fitting portion" here means the contact portion between the circular projection and the circular recess.

The medical container 1 illustrated in FIG. 1 uses the COP as the molten resin 6. In this way, by using the same materials for the upper member 2, lower member 4, and the molten resin 6, the sealing performance exhibited by the molten resin 6 becomes favorable to make it possible to firmly fix the upper member 2 and the lower member 4. However, the molten resin is not particularly limited as long as the molten resin is a thermoplastic hard resin having an excellent heat resistance and making it possible to conduct molding in which the thermal deformation is extremely reduced. Examples of the molten resin include resins listed as an example of the constituent material for the medical container, cyclic olefin based resins are preferable among them, and the COPs are particularly preferable.

[6] Production Method

The medical container 1 illustrated in FIG. 1 was produced by the method shown below. However, the method for producing the medical container of the present invention is not limited to the following method.

(1) The upper member 2 and the lower member 4 are separately injection-molded. At this time, molding is conducted so that the circular projection 30 of the lower member 4 has a larger diameter relative to the diameter of the circular recess 20 of the upper member 2.

(2) Next, the circular projection 30 of the lower member 4 is fitted to the circular recess 20 of the upper member 2 as illustrated in FIG. 4A and FIG. 4B (interference-fitting). At this time, the circular groove 42 is formed on the outer circumferential side of the medical container.

(3) Finally, the molten resin 6 is filled in the circular groove, and the fitting portion 40 between the circular projection 30 and the circular recess 20 is sealed from the outer circumferential side of the medical container as illustrated in FIG. 4C. By doing this, the upper member 2 and the lower member 4 can firmly be fixed with the molten resin 6. This process can be conducted by the method or the like in which the upper member and the lower member are fitted and then blocked, the molten resin is poured into the mold using the circular recess as a gate to conduct secondary molding (secondary injection).

INDUSTRIAL APPLICABILITY

The medical container of the present invention can suitably be utilized as a medical container such as, for example, a vial.

CROSS-REFERENCE TO RELATED APPLICATION

This application claims the priority of Japanese Patent Application No. 2014-127984 filed Jun. 23, 2014, which is incorporated herein by reference.

REFERENCE SIGNS LIST

1: medical container
2: upper member
4: lower member
6: molten resin
8: opening
10: bottom
12: neck
14: shoulder
16: body
18: cavity
20: circular recess
22: lower opening
24: cutout recess
26: tubular body
30: circular projection
32: cutout projection
40: fitting portion
42: circular groove
d: depth (of cutout recess)
h: height (of cutout projection)

The invention claimed is:

1. A bottomed tubular medical container made of a resin and continuously configured, comprising:
   a tubular neck having an opening formed on an upper end thereof;
   a trumpet-shaped shoulder whose diameter expands as the diameter goes toward a lower end of the shoulder; and
   a bottomed tubular body having a diameter larger than a diameter of the tubular neck and comprising a bottom at a lower end of the bottomed tubular body,
   wherein the medical container comprises:
      an upper member, which has a circular recess formed at a circular lower end surface of the upper member along a shape of the lower end surface thereof;
      a lower member, which has a circular projection formed at a circular upper end surface of the lower member along a shape of the upper end surface thereof; and
      a fitting portion between the circular projection and the circular recess, where an inner diameter of the circular recess is smaller than an outer diameter at a corresponding portion of the circular projection, and the circular projection and the circular recess are interference-fitted to each other,
   wherein each of a portion of the circular recess of the upper member and a portion of the circular projection of the lower member in the fitting portion is in a tapered shape in which a thickness of the each of the portion of the circular recess of the upper member and the portion of the circular projection of the lower member continuously decreases from a bottom toward an upper end side thereof,
   a tapered surface of the tapered-shaped portion of the circular projection facing the fitting portion is interference-fitted to a tapered surface of the tapered-shaped portion of the circular recess facing the fitting portion,
   each of the upper member and the lower member is in a shape obtained by vertically dividing the medical container along a direction perpendicular to a central axis of the medical container,
   the upper member is configured so as to comprise at least the tubular neck and the shoulder,
   the lower member is configured by a portion or a whole of the bottom tubular body, and
   the fitting portion between the circular projection and the circular recess is sealed with a molten resin applied from an outer circumferential side of the medical container, wherein the upper member and the lower member are fixed with the molten resin.

2. The medical container according to claim 1,
wherein the circular recess of the upper member is a cutout recess having a structure formed by cutting out an inner circumferential side of the upper member,
the circular projection of the lower member is a cutout projection formed by a residual portion left after cutting out an outer circumferential side of the lower member,
a circular groove is formed on an outer circumferential side of the medical container along a circumferential direction of the medical container by making a height of the cutout projection larger than a depth of the cutout recess,
the fitting portion between the cutout projection and the cutout recess is sealed with the molten resin from the outer circumferential side of the medical container by filling the molten resin into the circular groove, and
the upper member and the lower member are fixed with the molten resin.

3. The medical container according to claim 1,
wherein an interference thickness of the fitting portion, which is a difference between the inner diameter of the circular recess and the outer diameter of the circular projection, is in a range from 0.02 mm to 0.30 mm.

4. The medical container according to claim 1,
wherein a tapered angle of the tapered-shaped portion of each of the circular recess and the circular projection is in a range from 3° to 25°.

5. The medical container according to claim 1,
wherein the resin forming the medical container is at least one material selected from the group consisting of cyclic olefin based resins, polyethylene based resins, polypropylene based resins, polycarbonate based resins, and polyvinyl chloride based resins.

* * * * *